US008066645B2

(12) United States Patent
Krauter

(10) Patent No.: US 8,066,645 B2
(45) Date of Patent: Nov. 29, 2011

(54) BLOOD PRESSURE BLEED VALVE ASSEMBLY

(75) Inventor: Allan I. Krauter, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1500 days.

(21) Appl. No.: 11/507,238

(22) Filed: Aug. 21, 2006

(65) Prior Publication Data

US 2007/0060826 A1    Mar. 15, 2007

Related U.S. Application Data

(63) Continuation-in-part of application No. 11/225,744, filed on Sep. 13, 2005, now abandoned.

(51) Int. Cl.
    *A61B 5/02*    (2006.01)
(52) U.S. Cl. ........................ 600/498; 600/490
(58) Field of Classification Search .................. 600/498; 251/356
    See application file for complete search history.

(56) References Cited

U.S. PATENT DOCUMENTS

| | | |
|---|---|---|
| 3,131,716 A | 5/1964 | Griswold et al. |
| 3,254,671 A | 6/1966 | Berliner |
| 3,915,193 A | 10/1975 | Rutt |
| 3,955,595 A | 5/1976 | Modes |
| 4,072,171 A | 2/1978 | Nakazawa et al. |
| 4,332,275 A | 6/1982 | Brown |
| 4,416,287 A | 11/1983 | Riester et al. |
| 4,463,929 A | 8/1984 | Dantlgraber et al. |
| 4,587,974 A * | 5/1986 | Link .............................. 600/498 |
| 4,690,171 A | 9/1987 | Johnston |
| RE32,587 E | 2/1988 | Matsuura et al. |
| 4,791,956 A | 12/1988 | Kominami et al. |
| 5,143,077 A | 9/1992 | Kobayashi et al. |
| 5,220,925 A | 6/1993 | Hishida et al. |
| 5,251,655 A | 10/1993 | Low |
| 5,323,806 A | 6/1994 | Watari et al. |
| 5,833,620 A | 11/1998 | Murakami et al. |

FOREIGN PATENT DOCUMENTS

JP    5269090    10/1993

OTHER PUBLICATIONS

International Search Report for PCT/US06/32814, dated Jan. 4, 2008 (10 pages).

* cited by examiner

Primary Examiner — Patricia Mallari
(74) Attorney, Agent, or Firm — Roger P. Bonenfant

(57) ABSTRACT

A bleed flow valve assembly for venting air from a blood pressure cuff at relatively constant pressure decrease rate irrespective of cuff size includes a multiple chamber bleed valve and a multiple position control valve operatively associated therewith. A first end chamber is connected in pneumatic communication with the cuff and pneumatically sealed from a second central chamber by a first flexible diaphragm. A third end chamber is separated from the central chamber by a second flexible diaphragm. A variable flow area opening through the second diaphragm provides a flow path for controllably venting air from the second chamber to ambient pressure when the control valve is selectively positioned to connect the third chamber in pneumatic communication with ambient pressure. Air is vented from the cuff through the first chamber in regulated response to the pressure differential between the first chamber and the second chamber acting upon the first flexible diaphragm.

16 Claims, 4 Drawing Sheets

BLOOD PRESSURE BLEED VALVE ASSEMBLY

CROSS REFERENCE TO RELATED APPLICATION

This application is a continuation-in-part of U.S. patent application Ser. No. 11/225,744, filed Sep. 13, 2005 now abandoned, and entitled "Self-compensating Blood Pressure Bleed Valve", which application is assigned to the common assignee to which this application is subject to assignment, and the entire content of which is incorporated herein by reference.

FIELD OF THE INVENTION

This invention relates generally to the field of blood pressure measurement devices and, more particularly, to a nearly constant cuff pressure decrease rate valve for use in either manual or electronic blood pressure measurement devices.

BACKGROUND OF THE INVENTION

Blood pressure measurement devices, also referred to as sphygmomanometers, of the type commonly used to measure arterial blood pressure, include an inflatable sleeve, commonly referred to as a cuff, adapted to fit around a limb, e.g. an arm or leg, of a patient. The cuff includes an interior chamber that is in fluid communication with a device for selectively inflating the interior chamber of the cuff with pressurized air. A gage is operatively connected in fluid communication with the interior chamber of the cuff for monitoring the air pressure within the cuff. A bleed valve is also operatively connected in fluid communication with the interior chamber to permit selective depressurizing of the interior chamber when it is desired to deflate the cuff.

In a typical conventional manual sphygmomanometer, the interior chamber of the cuff is connected through a length of flexible tubing to a pneumatic bulb. In operation, the cuff is fitted, e.g. wrapped, about the arm of the patient and, once so positioned, the cuff is inflated by squeezing the pneumatic bulb to force air through the tubing into the interior chamber of the cuff. Once the interior chamber of the cuff has been inflated to a desired level in excess of the patient's anticipated systolic blood pressure, as indicated on the pressure gage, the cuff is deflated by opening the bleed valve to allow the pressurized air within the interior chamber of the cuff to vent slowly to atmosphere. A stethoscope is positioned under the cuff and over the patient's brachial artery to monitor the patient's arterial pulses as the cuff deflates, thereby allowing the systolic and diastolic blood pressures to be determined by listening for the Korotkoff sounds.

The systolic and diastolic blood pressure can also be measured oscillometrically by detecting the minute changes in the cuff pressure due to flow of blood through the brachial artery. This oscillometric measurement also utilizes an inflatable cuff and generally employs one or more pressure sensing devices, such as a transducer, to monitor the pressure within the interior chamber of the cuff. The transducer monitors both the average pressure in the cuff and the minute changes in the cuff pressure due to flow in the patient's artery as the cuff deflates. Electronic circuitry is provided that processes the signals from the pressure-sensing device and determines the systolic and diastolic blood pressures. A motor driven pump is usually provided to inflate the cuff. However, the inflation can be produced via a pneumatic bulb. Typically, a digital display is provided for displaying the systolic and diastolic blood pressures.

To obtain accurate measurements, it is necessary to deflate the inflated cuff at a relatively constant rate in the range of about 2 to about 3 millimeters mercury (2-3 mmHg) per second or about 2 to about 3 millimeters mercury (2-3 mmHg) per heartbeat. Maintaining a relatively constant bleed flow rate has been a problem when using many prior art sphygmomanometers, particularly when used by untrained personnel. For example in conventional manual sphygmomanometers, a typical vent valve has an air passage through which the flow of air may be adjusted by selectively restricting the flow area by manipulation of a thumbscrew. The thumbscrew is tightened down to fully close the vent valve passage when the cuff is being inflated. With the cuff inflated to the desired starting pressure, the user manually turns the thumbscrew to slightly open the vent valve passage to initiate deflation of the cuff. The user also monitors the patient's artery using a stethoscope to listen for the aforementioned Korotkoff sounds to detect when the systolic pressure and the diastolic pressure have been reached. As the cuff deflates, the user should follow the decrease in cuff pressure as registered on the pressure gauge and should continually adjust the vent thumb screw to increase the flow area through the vent valve passage as the pressure in the cuff decreases in an attempt to maintain a nearly constant bleed rate. The user should maintain this rate within the desired rate range, while at the same time continuing to concentrate on listening for the characteristic Korotkoff sounds to detect the systolic and diastolic blood pressures. It is difficult to manually maintain the desired linear pressure decrease as the cuff deflates by adjusting a thumbscrew even under ideal conditions. It is even more difficult to do so when attempting to listen for the arterial sounds. Once the cuff pressure has dropped to the diastolic pressure point, the user must then further adjust the thumbscrew to fully open the vent passage, thereby providing a rapid final deflation of the cuff to ensure patient comfort.

An electronic blood pressure measurement apparatus can be designed with linear cuff pressure decrease. Such an apparatus may comprise a valve that vents the interior chamber of the inflated cuff through a port whose flow area is controlled electronically. To deflate the cuff, the controller selectively opens the valve. This selective opening is needed to compensate for the airflow behavior of a fixed area port. With a fixed area port, the vent flow rate varies as a function of the pressure differential across the port at any given time in the venting process. As the pressure within the interior chamber continuously decreases during the deflation process, the pressure differential—that is, the difference between the air pressure within the interior chamber of the cuff and ambient pressure—also continuously decreases. Therefore, since the pressure differential across the vent port is continuously decreasing, the flow rate does not remain relatively constant to provide the desired 2-3 mmHg/sec rate during the deflation process, but rather continuously decreases.

It is well known in the art that the inflated volume of the pressure chamber of the cuff affects the bleed rate through a conventional fixed area orifice bleed valve. For example, a cuff for a large adult typically has a pressure chamber having a length of approximately 27 centimeters and a width of approximately 12.5 centimeters, while a cuff for a small child typically has a pressure chamber having a length of approximately 13 centimeters and a width of approximately 5 centimeters. The fact that the inflated volume of the adult cuff is many times as great as the inflated volume of the child cuff has a substantial impact upon the rate of pressure decrease in the respective cuffs for deflation through a bleed valve having a fixed flow area opening. The larger volume cuff exhibits a slower pressure decrease rate at a given inflation pressure than the smaller volume cuff exhibits. As discussed above, this pressure decrease rate does not remain constant as the cuff deflates, but rather decreases as the cuff deflates due to the drop in pressure within the cuff.

In U.S. Pat. No. 4,587,974, Link discloses a pressurizing and depressurizing design for a blood pressure cuff with the objective of controlling the cuff inflation or deflation process at a substantially linear rate independent of the size of the cuff in use. In a preferred arrangement, the disclosed device includes a housing defining an internal volume divided by a wall supporting a flexible diaphragm. This division produces a control chamber and an active chamber, the wall and diaphragm forming a boundary therebetween. The active chamber is in pneumatic communication with the blood pressure cuff and with a vent passage to ambient surroundings. The control chamber is in pneumatic communication with the active chamber via an opening in the division wall, the opening forming pneumatic restrictor. The flexible diaphragm moves in response to the pressure differential between the active chamber and the control chamber to selectively open and close the outlet from the active chamber to the vent passage. In depressurizing the cuff, air from the cuff passes into the active chamber causing the diaphragm to flex away from the vent passage and toward the control chamber, thereby opening the vent passage to allow air to vent from the active chamber to ambient surroundings. Simultaneously, air passes between the control chamber and the active chamber through the restrictor opening between the chambers so as to rebalance the pressures between the chambers. In this manner, the diaphragm fluctuates to and fro relative to the outlet to the vent passageway so as to continuously open and close the vent passageway. This controls the rate at which the cuff deflates through the active chamber to produce a substantially linear rate determined by the flexing characteristic of the diaphragm.

However, the device disclosed in U.S. Pat. No. 4,587,974 does not provide for the rapid deflation of the cuff directly to ambient pressure for patient comfort once the diastolic pressure point has been reached. Additionally, when the vent valve of the device is opened at the beginning of the deflation process, an abrupt drop in cuff pressure can initially occur until the diaphragm responds sufficiently to cause closure of the vent port. Such an abrupt decrease can be relatively large, in particular for small cuffs, and disruptive of the blood pressure measurement process. Further, after this abrupt pressure decrease, a relatively large differential pressure may exist across the diaphragm while the air flows from the control chamber through the flow restrictor and into the active vent chamber to reduce the pressure differential. The deflation process can not start properly until this pressure balancing is completed. Once the deflation process does begin, the initial deflation of the cuff proceeds slowly until the eventual linear steady state rate is achieved.

In the device disclosed in the U.S. Pat. No. 4,587,974, the time required to the pressurize the system is lengthened because air passing into the control chamber must first pass through the flow restrictor, which causes a time delay between the time the cuff is pressurized and the control chamber is pressurized to cuff pressure. If the user doesn't wait until the pressure in the control volume reaches that in the cuff, there is an abrupt decrease in cuff pressure (which can be large for small cuffs) when the closure valve is opened to start the cuff deflation process. Also, the cuff pressure backs off while the pressure within the control chamber of the bleed valve equalizes with the cuff pressure, resulting in a decrease in cuff pressure, which may be large for small cuffs, requiring additional pumping action to return the cuff pressure to the desired starting pressure level.

The aforementioned deficiencies complicate the design of the device. For example, to minimize the aforementioned effects, the diaphragm must be selected to have low inertia. The diaphragm must also not require a high pressure differential across it to move the valve stem relative to the outlet vent opening through the operating range. The diaphragm must also provide sufficient flow area at the outlet port so that rapid deflation of large cuffs is possible.

SUMMARY OF THE INVENTION

It is an object of one aspect of the invention to provide a self-compensating bleed valve assembly exhibiting a relatively constant pressure decrease rate.

It is an object of one aspect of the invention to provide a self-compensating bleed valve assembly that vents at a relatively constant pressure decrease rate that is independent of the size of the cuff in use.

It is an object of a further aspect of the invention to provide a method for venting air from a blood pressure cuff at a relatively constant cuff pressure change rate independent of the size of the cuff.

In an aspect of the invention, a bleed valve assembly is provided for self-controlling the pressure change rate during the deflation of an inflated blood pressure cuff to facilitate the blood pressure measurement process. The bleed valve assembly includes a bleed valve and a control valve operatively associated therewith. The bleed valve defines an interior chamber that is sectioned into a first pressure chamber and a second pressure chamber by a first flexible diaphragm extending across the interior chamber of the bleed valve. The first diaphragm provides a seal between the first pressure chamber on a first side of the first diaphragm and the second pressure chamber on a second side of the first diaphragm. A second diaphragm sections the second pressure chamber from a third pressure chamber. This third pressure chamber is on a second side of said second diaphragm, the first side of which is on the second pressure chamber. A first vent passage, having a regulated flow area outlet to ambient pressure from the first pressure chamber of the bleed valve, provides a flow path for venting the first pressure chamber to the exterior of the bleed valve. A second vent passage opens from the second pressure chamber of the bleed valve to the third pressure chamber of the bleed valve and has a variable flow area. A selectively positionable control valve is operatively associated with and connected in pneumatic communication with the three sections of the interior chamber of the bleed valve. The control valve is positionable in a first position for equalizing the pressures in the three pressure chambers, in a second position for venting the blood pressure cuff through the first vent passage via the first pressure chamber and for venting the second pressure chamber to ambient pressure at a substantially constant pressure decrease rate through the second vent passage, and in a third position bypassing the bleed valve for rapidly venting the blood pressure cuff to ambient pressure or for rapidly decreasing the cuff pressure during a portion of the blood pressure measurement process.

In an embodiment of the bleed valve assembly, the second flexible diaphragm is disposed within the interior chamber of the bleed valve in spaced relationship with the first diaphragm to establish the third pressure chamber. In this embodiment, the second pressure chamber extends between the first diaphragm and the second diaphragm, and the third pressure chamber lies on the opposite side of the second diaphragm. The second diaphragm has a centrally located hole passing therethrough that provides pneumatic communication between the second pressure chamber and the third pressure chamber. An axially elongated rod having a tapered distal tip is positioned within the hole in the second flexible diaphragm. During the cuff deflation mode, a pressure differential exists between the second pressure chamber and the third pressure chamber. This pressure differential causes the second flexible diaphragm to move axially relative to the tapered distal tip, and in operative association with the tapered distal tip, to form a variable area opening between the second and third pressure chambers. In an embodiment, the axially elongated rod may be selectively positioned axially within the hole in the second flexible diaphragm to provide an annular orifice between the rod and the second flexible diaphragm having a desired maximum flow area when the second flexible diaphragm is in an unflexed state. In an embodiment, the tapered distal tip of the axially elongated rod is an extension of a rod that tapers linearly from a maximum cross-sectional area at its proximal base end to a minimum cross-sectional area at its distal end.

In the dual diaphragm embodiment of the bleed valve assembly, the selectively positionable control valve has a first port connected in pneumatic communication with the blood pressure cuff, the first pressure chamber of the bleed valve, and the air pump. A second port is in pneumatic communication with ambient pressure. A third port is in pneumatic communication with the third pressure chamber of the bleed valve and a fourth port is in pneumatic communication with the second pressure chamber of the bleed valve. During the cuff inflation mode, the control valve is positioned in a first position wherein the first, third and fourth ports are connected in pneumatic communication for pressurizing and equalizing the pressure within the first, second and third pressure chambers of the bleed valve. During the cuff deflation mode, the control valve is in a second position wherein the second port and the third port are connected in pneumatic communication with each other for venting the third pressure chamber to ambient pressure at a substantially constant bleed rate through the second vent passage. Also during this mode the first and fourth ports are closed. The first pressure chamber and the connected cuff are simultaneously vented to ambient pressure at a substantially constant pressure decrease rate through the first vent passage as is detailed hereinbelow. During a final cuff deflation mode, in which the cuff pressure is rapidly vented to ambient pressure, the control valve is in a third position wherein the first port, the second port, and the fourth ports are connected in pneumatic communication, which rapidly vents the blood pressure cuff to ambient pressure.

In an aspect of the invention, a method is provided for venting air from a blood pressure cuff inflated to a cuff pressure through a bleed valve at a relatively constant cuff pressure decrease rate that is independent of cuff size. The method comprises the steps of: providing a first pressure chamber and a second pressure chamber within the bleed valve in pneumatically sealed relationship; pressurizing the first pressure chamber and the second pressure chamber to the cuff pressure; establishing air flow communication between the inflated cuff and the first pressure chamber; isolating the second pressure chamber from the cuff and establishing pneumatic communication between the second pressure chamber and ambient pressure; controllably venting air from the second pressure chamber at a relatively constant bleed rate in response to a pressure differential between the second pressure chamber and ambient pressure; and venting air from the first pressure chamber to ambient pressure in regulated response to a pressure differential between the first chamber and the second pressure chamber, whereby the pressure within the cuff decreases at a relatively constant cuff pressure change rate that is independent of the size of the cuff.

To controllably vent air from the second pressure chamber, a variable area airflow opening is provided between the second pressure chamber and ambient pressure. The area of the opening self-adjusts in response to the pressure differential between the second pressure chamber and ambient pressure, with the area of the opening increasing as the pressure differential between the second pressure chamber and ambient pressure decreases. To vent air from the first pressure chamber in regulated response to a pressure differential between said first chamber and said second pressure chamber, an air flow passage is provided between said first pressure chamber and ambient pressure and the flow area into the air flow passage is regulated in response to the pressure differential between the first pressure chamber and the second pressure chamber.

BRIEF DESCRIPTION OF THE DRAWINGS

For a further understanding of these and objects of the invention, reference is made to the following detailed description of the invention which is to be read in connection with the accompanying drawing, where.

DETAILED DESCRIPTION OF THE INVENTION

Figure 1:
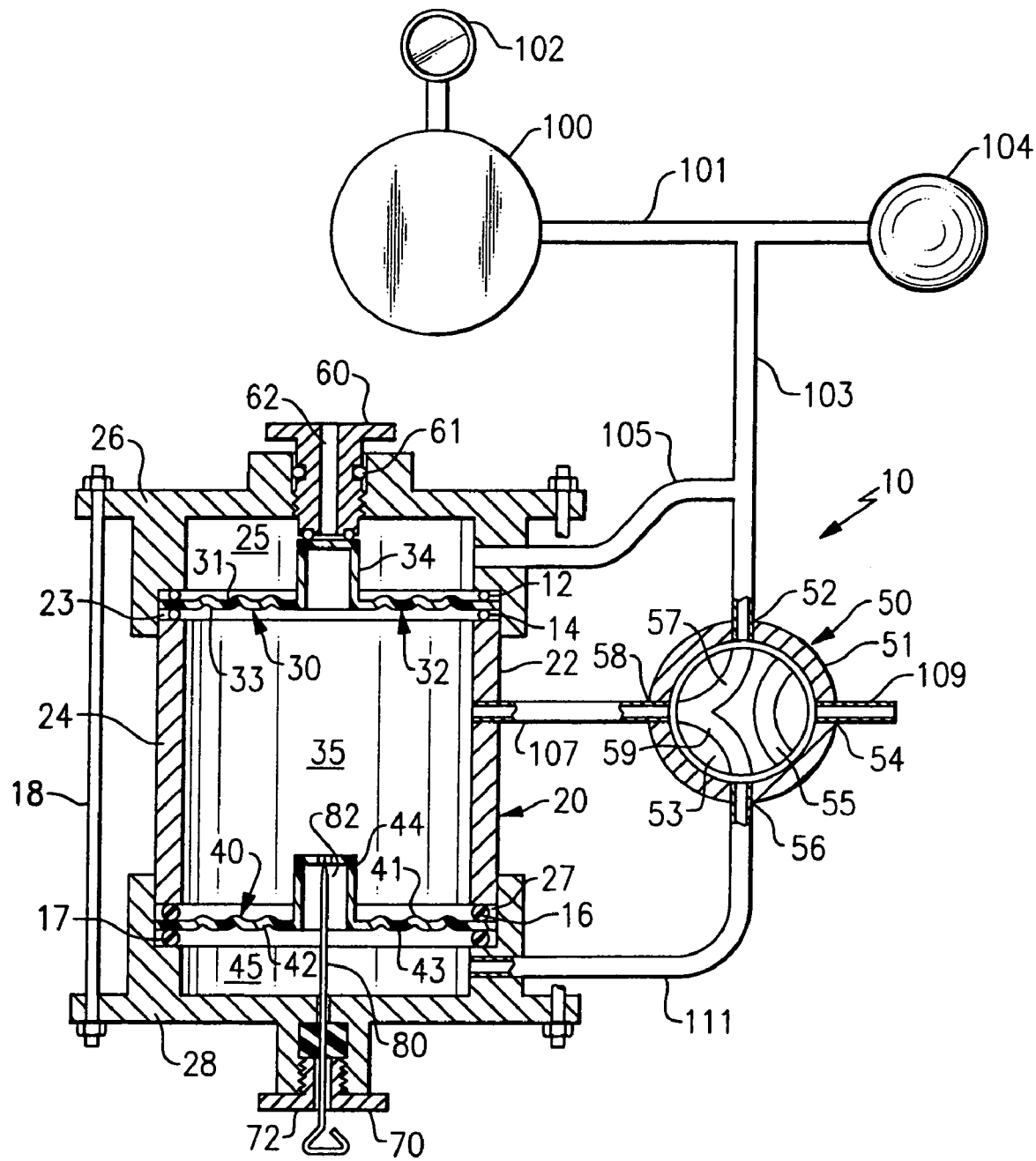
FIG. 1 is an elevation view, partly in section, of an exemplary embodiment of the bleed valve assembly of the invention positioned as during inflation of an associated blood pressure cuff.
Figure 2:
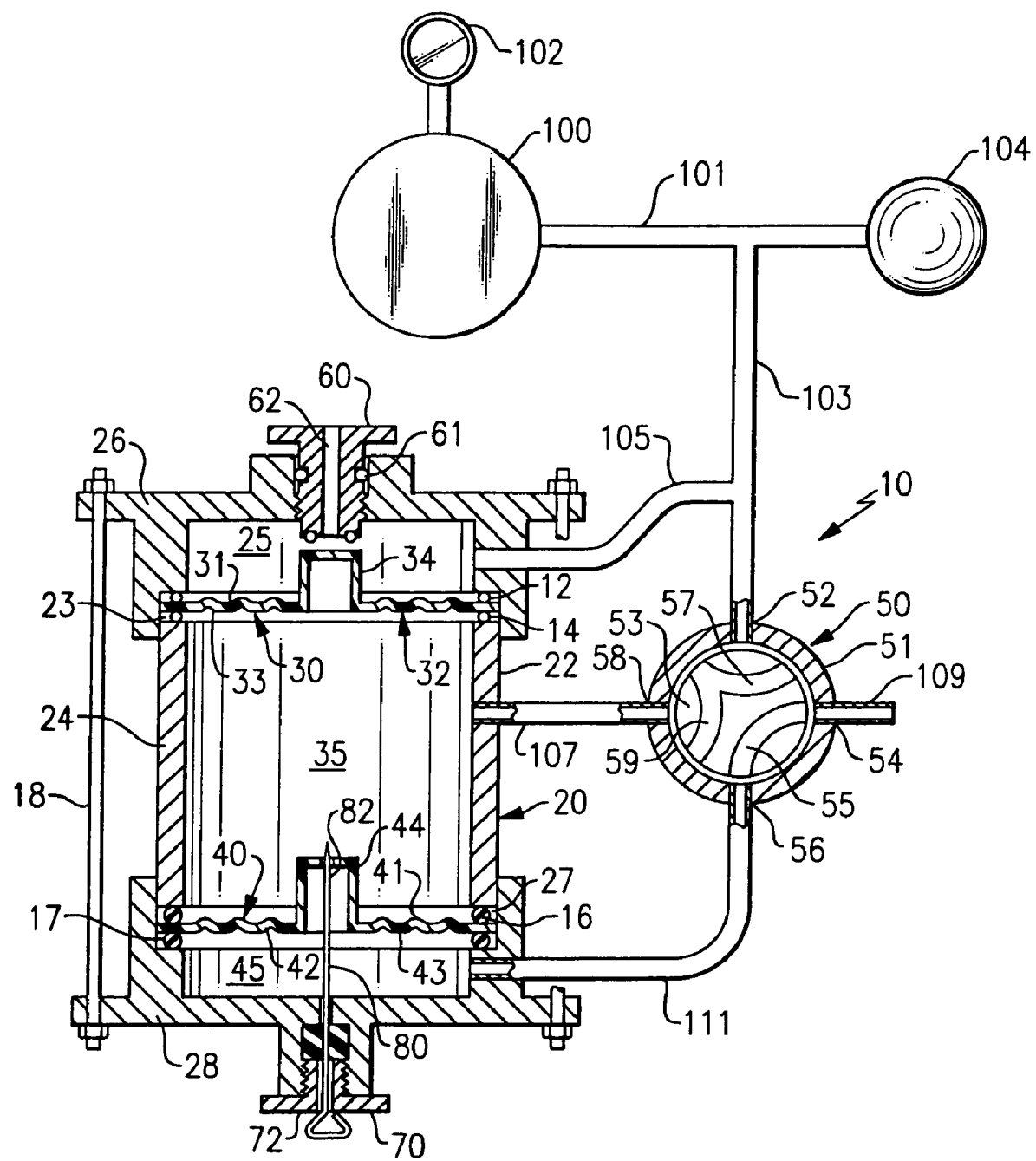
FIG. 2 is an elevation view, partly in section, of the exemplary embodiment of the bleed valve assembly of the invention positioned as during controlled deflation of an associated blood pressure cuff.
Figure 3:
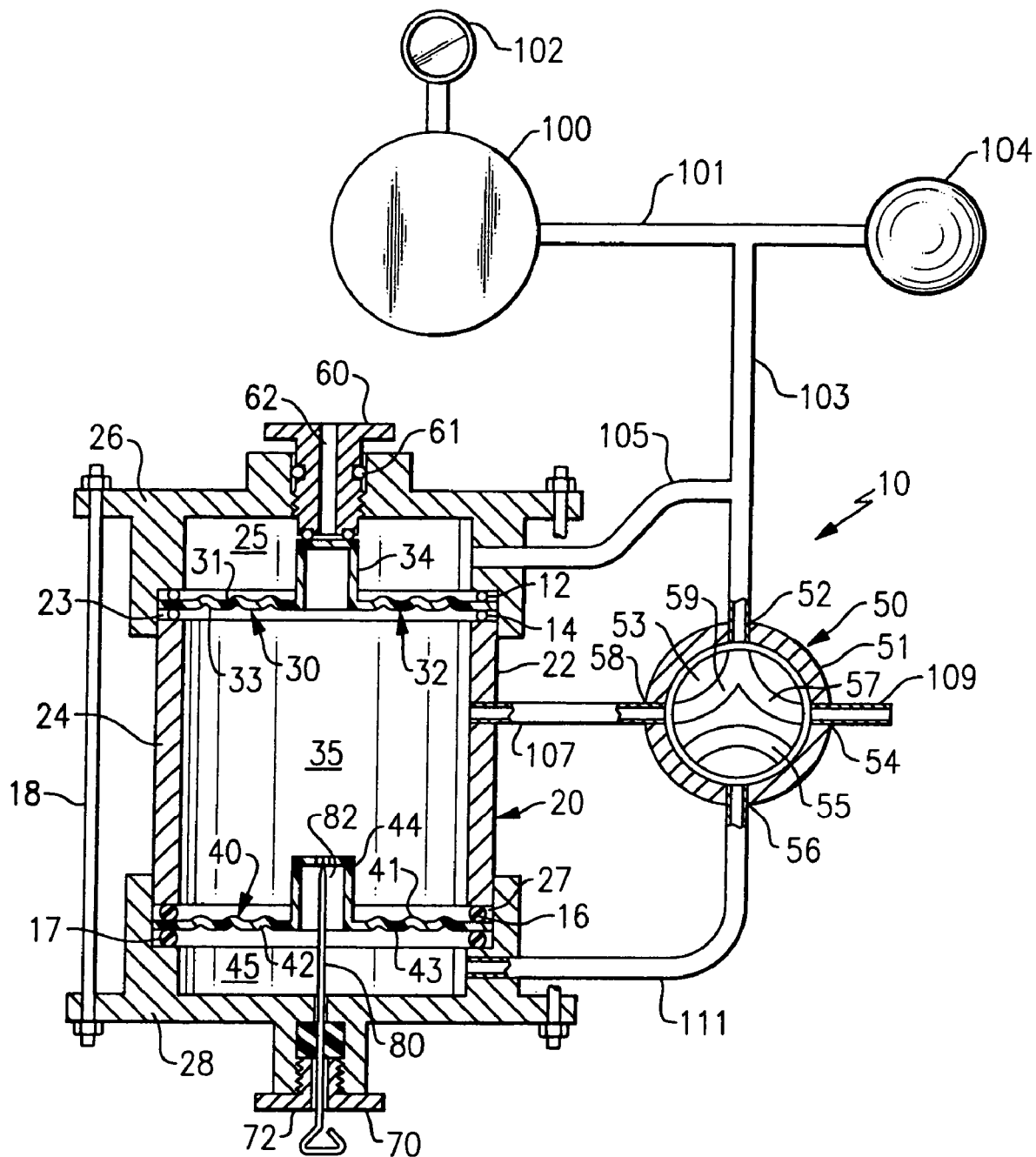
FIG. 3 is an elevation view, partly in section, of the exemplary embodiment of the bleed valve assembly of the invention positioned as during rapid deflation of an associated blood pressure cuff.

Referring now to FIGS. 1, 2 and 3, in particular, an exemplary embodiment of the bleed valve assembly 10 of the invention 10 includes a bleed valve 20 and a selectively positionable control valve 50 operatively associated the with bleed valve 20. The bleed valve 20 includes a three-part housing 22 defining an interior chamber having a fixed internal volume, which is divided into three separate chambers by a pair of spaced apart flexible diaphragms 30 and 40. Each of the flexible diaphragms 30 and 40 is a relatively thin disk having an annular portion 32, 42 and a centrally located, thimble-like portion 34, 44 that extends outwardly from the front side 31, 41 of the annular portion of the respective diaphragms. The diaphragms 30 and 40 may be made from metal, such as copper, aluminum, tin or the like, or an elastoplastic material. The diaphragms may also be made flat; i.e., with in-plane central discs replacing the thimble-like portions 34, 44.

The first flexible diaphragm 30 extends across the interior chamber of the bleed valve 20 and sections the interior chamber into a first pressure chamber 25 on the front side 31 of the first diaphragm 30 and a second pressure chamber 35 on the rear side 33 of the first diaphragm 30. The first pressure chamber 25 is pneumatically sealed from the second pressure chamber 35 by the first diaphragm 30, which is supported on a pair of seals 12 and 14 extending circumferentially around the edge and on each surface of the first diaphragm 30. The seals 12 and 14 are disposed in a land 23 in an upper end cap 26 of the housing 22, with the O-ring 12 disposed superadjacent the front side 31 of the first diaphragm 30 and the O-ring 14 disposed subadjacent the rear side 33 of the first diaphragm 30.

The second flexible diaphragm 40 extends across the second pressure chamber 35 of the bleed valve 20 to establish a third pressure chamber 45 on the rear side 43 of the second diaphragm 40. The second diaphragm 40 is supported about its radially outward surfaces in a land 27 in a lower end cap 28 of the housing 22 between seals 16 and 17. The seals 16 and 17 extend circumferentially around the edge and on each surface of the second diaphragm 40. Seals 16 and 17 are disposed superadjacent the front side 41 and subadjacent the rear side 43, respectively, of the second diaphragm 40. The seals 16 and 17 provide a pneumatic seal between the central pressure chamber 35 and the third pressure chamber 45. The second diaphragm 40 has a centrally located hole 46, FIGS. 5 and 7, passing therethrough that provides a fluid flow path, establishing pneumatic communication between the second pressure chamber 35 and the third pressure chamber 45.

The second pressure chamber 35, which defines a reference volume, lies between the spaced apart diaphragms 30 and 40. The first pressure chamber 25 is located on the front side of the first diaphragm 30. The third pressure chamber 45 is located on the rear side of the second diaphragm 40. The reference volume, which remains substantially constant throughout the cuff deflation process, is relatively large in comparison to the respective volumes of the first and third pressure chambers. In reference to the depicted embodiment of the bleed valve 20, the first pressure chamber 25 is also be referred to herein as the upper pressure chamber, the second pressure chamber 35 is referred to herein as the central pressure chamber, and the third pressure chamber 45 is referred to herein as the lower pressure chamber.

The housing 22 of the exemplary embodiment of the bleed valve 20 includes a cylinder 24 having a central bore extending axially therethrough, the upper end cap 26 mounted to the upper end of the cylinder 24, and the lower end cap 28 mounted to the lower end of the cylinder 24. The upper end cap 26 and lower end cap 28 are secured to the respective upper and lower ends of the cylinder 24 by at least two clamp screws 18 extending between the respective flanges of the end caps 26 and 28. The aforementioned land 23, in which the first flexible diaphragm 30 is supported, is formed in the end cap 26. Similarly, the aforementioned land 27, in which the second flexible diaphragm 40 is supported, is formed in the end cap 28.

The upper end cap 26 has a central bore extending therethrough that is internally threaded to receive an end fitting 60. The end fitting 60 has an axially extending shaft having a threaded tip adapted to be threaded into the central bore of the end cap 26. A circumferential seal 61, for example an O-ring seal, is disposed within the central bore of the end cap 26 to provide a seal between the internal surface of the central bore and the outer surface of the shaft of the end fitting 60. Additionally, the end fitting 60 has an axial bore 62 extending axially therethrough having an opening 64 into the upper pressure chamber 25. The central bore 62, extending axially through the end fitting 60, forms a first vent passage for venting fluid from within the upper pressure chamber 25 directly to ambient pressure exteriorly of the bleed valve 20. The outlet to the central bore 62 has a regulated flow area. An elastomeric ring 66, FIGS. 4 and 6, such as for example an O-ring, is carried on the end face of the end fitting 60 and extends circumferentially about the outlet to the central bore 62. The end fitting 60 is threaded into the central bore of the end cap 26 sufficiently far for the O-ring to contact and seal against the surface of the thimble-like outward projection 34 of the first flexible diaphragm 30. This sealing is produced via preloading of the diaphragm 30 by the O-ring 60.

The lower end cap 28 also has a central bore extending therethrough that is internally threaded to receive an end fitting 70. The end fitting 70 has an axially extending threaded shaft adapted to be threaded into the central bore of the end cap 28. The end fitting 70 has an axial bore 72 extending axially therethrough in which an axially elongated rod 80 is supported on an elastomeric bushing 71, for example a compression seal, which is disposed within the central bore of the end cap 28. The bushing 71 not only provides support for the axially elongated rod 80, but also seals the region between the rod 80 and the surrounding interior wall of the central bore of the end cap 28 so that fluid does not leak therethrough from the third pressure chamber 45 to the ambient pressure environment exterior of the bleed valve 20.

Figure 5:
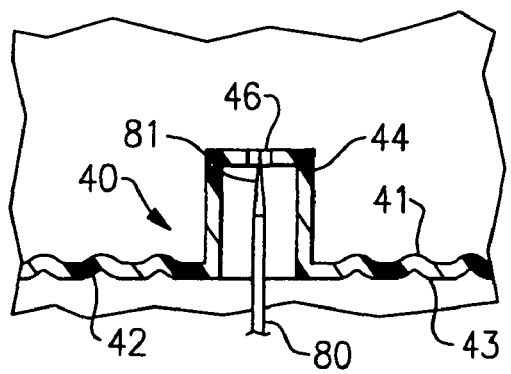
FIG. 5 is an exploded elevation view showing the second diaphragm of FIG. 1 in its non-flexed position.
Figure 7:
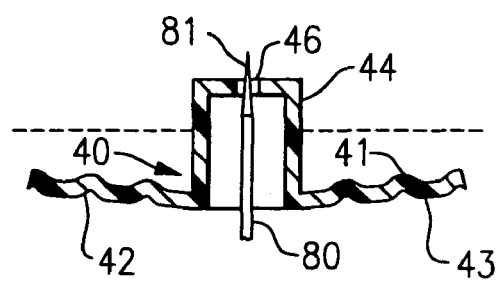
FIG. 7 is an exploded elevation view showing the second diaphragm of FIG. 2 in its flexed position.

The axially elongated rod 80, which need not be axisymmetrical or cylindrical, has a tapered tip 82, FIGS. 5 and 7, at its distal end. The tapered tip may comprise a generally conical extension of the rod that tapers inwardly from a maximum diameter at its base end to a minimum diameter at its end. This taper need not be conical, and may be created by cutting through the rod at an angle. The rod 80 extends axially through the end fitting 70 into the lower pressure chamber 45 so that the tapered tip 82 of the rod 80 is positioned within the hole 46, FIGS. 5 and 7, in the second flexible diaphragm 40. In operative association, the rod 80, in particular the tapered tip 82 of the rod 80, and the hole 46 in the second flexible diaphragm 40 form an annular orifice opening between the central pressure chamber 35 and the lower pressure chamber 45, whereby fluid may pass from the central pressure chamber into the lower pressure chamber. As is explained further hereinafter, as the second flexible diaphragm 40 flexes in response to a pressure differential being present across this diaphragm due to a pressure difference existing between the pressure in the central pressure chamber 35 versus the pressure in the lower pressure chamber 45. The hole 46 in the top of the thimble-like outward projection 44 on the second diaphragm 40 thereby translates axially relative to the tapered tip 82 in response to this pressure differential. As a result, the flow area through the annular orifice opening formed between the rod 80 and the second diaphragm 40 varies.

As noted hereinbefore, the bleed valve assembly 10 includes a selectively positionable control valve 50 operatively associated with the bleed valve 20. In the exemplary embodiment of the bleed valve assembly of the invention depicted in FIGS. 1-3, the control valve 50 is a three-position valve including a housing 51 having four ports 52, 54, 56 and 58, and a rotatable disc 53 disposed within the housing 51. The rotatable disc 53 has internal fluid passages 55, 57 and 59 formed therein. The control valve 50 is connected in pneumatic communication with the bleed valve 20, blood pressure cuff 100, and cuff inflation pump 104 via the aforementioned ports. As depicted in FIGS. 1-3, the blood pressure cuff 100 and the cuff inflation pump 104 are connected in pneumatic communication to the first port 52 of the control valve 50 via conduits 101 and 103. Additionally, the upper pressure chamber 25 of the bleed valve 20 is also connected in pneumatic communication to the first port 52 of the control valve 50 through conduit 105 via conduit 103. The second port 54 of the control valve 50 is directly in pneumatic communication with ambient pressure either through conduit 109 or by simply via an opening directly through the housing 51 to the environment exterior of the control valve 50. The third port 56 of the control valve 50 is connected in pneumatic communication to the lower pressure chamber 45 of the bleed valve 20 via conduit 111 and the fourth port 58 of the control valve 50 is connected in pneumatic communication to the central pressure chamber 35 of the bleed valve 20 via conduit 107. Each of the conduits 101, 103, 105, 107,109 and 111 may be flexible tubes of the type conventionally used for blood pressure tubing.

The control valve 50 may be selectively positioned in one of three positions during the blood pressure measurement process. During inflation of the blood pressure cuff 100, the control valve 50 is positioned in a first position, as shown in FIG. 1, wherein blood pressure cuff 100, the cuff inflation pump, the upper chamber 25, the central chamber 35, and the lower chamber 45 are all connected together in pneumatic communication via the internal passages 57 and 59 of the control valve 50. In this first position, the rotatable disc 53 is positioned such that the internal passages 57 and 59 thereof interconnect ports 52, 56 and 58 to form fluid flow passages therebetween as illustrated in FIG. 1. With the control valve 50 in this first position during the cuff inflation mode, the air pressure in each of the upper, central, and lower pressure chambers increases as the cuff pressure increases, thereby equalizing the pressures in first or upper pressure chamber 25, the second or central pressure chamber 35 and the third or lower pressure chamber 35 with the pressure in blood pressure cuff 100. In this first position, internal passage 55 is not in registration with any of the control valve ports and is therefore not functional.

In the cuff deflation mode, the control valve 50 is positioned in a second position, as shown in FIG. 2, for venting the blood pressure cuff 100 at a substantially constant pressure decrease rate. To position the control valve 50 in this second position, the disc 53 is rotated 45 degrees clockwise from the first position to bring the internal passage 55 in registration with ports 54 and 56. This 45 degree rotation establishes a fluid flow passage connecting ports 54 and 56. With the control valve 50 in this second position during the cuff deflation mode, the lower or third pressure chamber 45 is connected via conduit 111 and passage 55 to ambient pressure at port 54. Also in this second position, the internal passages 57 and 59 are not in registration with any of the control valve ports and are therefore not functional. More specifically, the control valve ports 52 and 58 are closed in this second position.

In the final cuff deflation mode, the control valve 50 is positioned in a third position, as shown in FIG. 3, for rapidly venting the blood pressure cuff 100 to ambient pressure and bypassing the bleed valve 20. To position the control valve 50 in this third position, the disc 53 is rotated an additional 45 degrees clockwise from the second position to bring the internal passage 57 in registration with ports 52 and 54, thereby establishing a fluid flow passage connecting ports 52 and 54. In this third position of the control valve, internal passage 59 is in registration with ports 52 and 58, thereby establishing a fluid flow passage connecting ports 58 and 54. With the control valve 50 in this third position during the final cuff deflation mode, the blood pressure cuff 100 is connected directly via conduits 101, 103, and internal passage 57 with ambient pressure at port 54. In addition, the second pressure chamber 35 is likewise connected directly with ambient pressure at port 54. In this third position, internal passage 55 is again not in registration with any of the control valve ports and is therefore not functional.

The operation of the bleed valve assembly 10 of the invention is described in connection with the process of taking a patient's blood pressure. After the blood pressure cuff 100 has been wrapped about the patient's arm (not shown), the operator inflates the blood pressure cuff 100 by pumping the hand pump 104, also referred to as a pressure bulb, as in conventional practice. Prior to initiating this inflation of the cuff 100, the operator places the control valve 50 of the bleed valve assembly 10 of the invention in its first position as shown in FIG. 1 by means of a hand dial (not shown) or other positioning device that operates to rotate the disc 53 amongst the three control valve positions selectable by the operator. With the control valve 50 in this first position, air supplied by pumping the hand pump 104 not only inflates the blood pressure cuff 100, but also simultaneously passes through conduits 103 and 105 to pressurize the upper pressure chamber 25 of the bleed valve 20; through conduit 103, control valve internal passage 57 and conduit 107 to pressurize the central pressure chamber 35 of the bleed valve 20; and through conduit 103, control valve internal passages 57 and 59, and conduit 111 to pressurize the lower pressure chamber 45.

Figure 4:
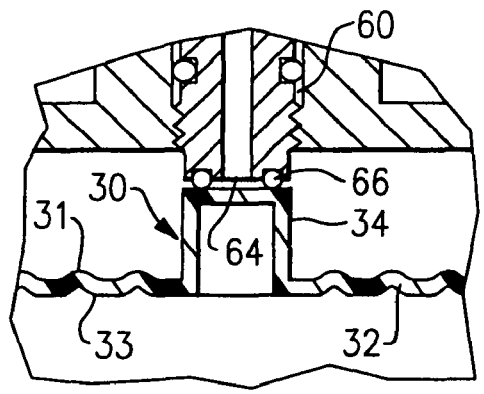
FIG. 4 is an exploded elevation view showing the first diaphragm of FIG. 1 in its non-flexed position.

In this manner, each of the upper, central and lower pressure chambers are simultaneously pressurized to the same pressure, which is also the pressure to which the cuff 100 is pressurized. As the pressures on each side of the first (upper) flexible diaphragm 30 are equal, and as the effective pressure area below the diaphragm is slightly larger than that above the diaphragm, the top surface of central portion 34 of the first diaphragm 30 remains in contact against the O-ring 66, as is shown in FIG. 4. The first vent passage formed by the central bore 62 through the end fitting 60 is thereby closed, and no fluid escapes the upper pressure chamber 25 during the cuff inflation process. Since the pressures on each side of the second (lower) flexible diaphragm 40 are equal, the second diaphragm 40 remains in its unflexed state. As a result, the relative positioning of the hole 46 in the central portion of the second diaphragm 40 with respect to the tapered tip 82 of the rod 80 remains at its preset position as is illustrated in FIG. 5. Therefore, the size of the annular orifice opening between the tapered tip 82 of the rod 80 and the surrounding hole 46 is unchanged. Because the pressures in the central and lower pressures are equal, no fluid flow occurs through the orifice opening.

Once the blood pressure cuff 100 has been inflated to a desired pressure level (typically a pressure in excess of the patient's estimated systolic blood pressure) as indicated on pressure gage 102, which is operatively associated with the cuff 100 in a conventional manner, the operator changes the positioning of the control valve 50 from its first position to its second position. This is accomplished by rotating a hand dial (not shown), and therewith the disc 53, clockwise 45 degrees. With the control valve 50 in this second position, ports 52 and 58 are now closed, thereby closing off the cuff 100, the upper pressure chamber 25, and the central pressure chamber 35. Additionally, port 56 is now connected internally to port 54 via internal flow passage 55, thereby establishing direct pneumatic communication between the lower pressure chamber 45 and ambient pressure through conduit 111, internal passage 55, and port 54. With the lower pressure chamber 45 now in direct communication with ambient pressure, the pressure within the lower pressure chamber 45 drops to a level effectively at ambient pressure. Air vents from the central pressure chamber 35 through the orifice opening formed between the tapered tip 82 of the rod 80 and the surrounding hole 46, FIG. 5, in the thimble-like portion 44 of the second diaphragm 40. The air then passes through the third pressure chamber 45, conduit 111, control valve internal passage 55, and out of port 54 to ambient pressure, which collectively form a second vent passage for the bleed valve 20.

When the air begins to vent from the central pressure chamber 35, the pressure differential between the central pressure chamber 35 and the lower pressure chamber 45 is relatively large. This pressure differential acts upon the second diaphragm 40 to flex the second diaphragm 40 downwardly. As a result, the hole 46 moves downwardly along the tapered tip 82 of the rod 80, as illustrated in FIG. 7, causing the flow area through the orifice opening between the rod 80 and the surrounding hole 46 to decrease, and thereby restricts the flow rate of air passing from the central pressure chamber 35 into the lower pressure chamber 45. As the pressure within the central pressure chamber 35 decreases, the pressure differential across the second diaphragm also decreases. As a result, the hole 46 in the central portion 44 of the second diaphragm 40 moves upwardly along the tapered tip 82 of the rod 80 while the second diaphragm 40 relaxes back toward its original unflexed state. This upward movement of the hole 46 relative to the tapered tip 82 of rod 80 results in a continuous increase in the flow area of the orifice opening between the rod 80 and the surrounding hole 46 as the pressure within the central pressure chamber 35 decreases. Therefore, as the pressure within the central pressure chamber 35 decreases, the flow area through the orifice opening increases, thereby compensating for the decrease in the pressure within the central pressure chamber 35 so that the rate of pressure drop within the central pressure chamber 35 remains substantially constant.

Figure 6:
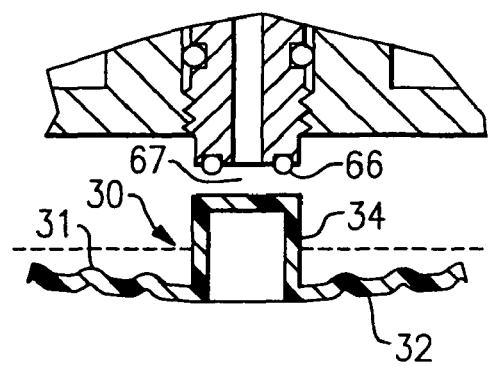
FIG. 6 is an exploded elevation view showing the first diaphragm of FIG. 2 in its flexed position.

During the deflation process, the upper pressure chamber 25 is in pneumatic communication with the blood pressure cuff 100 and is pneumatically sealed from the central pressure chamber 35. This pressure in the upper pressure chamber 35 is substantially equal to the cuff pressure. Thus, as the pressure within the central pressure chamber 35 drops, a pressure differential builds across the first (upper) flexible diaphragm 30. This pressure differential acts to flex the first diaphragm 30 downwardly (i.e., toward the central pressure chamber 35) and out of contact with the O-ring 66 at the first vent passage formed by axial bore 62 that extends through the end fitting 60 in the upper end cap 26. When the top surface of the thimble-like portion 34 of the first diaphragm 30 moves away from the O-ring 66, as illustrated in FIG. 6, an annular gap 67 opens therebetween. Air vents through this gap from the blood pressure cuff 100 through the upper pressure chamber 25 into and through conduit 62 directly to ambient pressure exteriorly of the bleed valve 20, whereby the blood pressure cuff begins to deflate. The annular gap 67 continuously adjusts such that the pressures in pressure chambers 25 and 35 remain substantially equal. For example, should the pressure in pressure chamber 25 fall below that in pressure chamber 35, the diaphragm 30 moves upwards, thereby closing the annular gap and decreasing the flow of air to ambient pressure.

Air from the pressure chamber 35 bleeds through the variable area orifice formed between the rod 80 and the hole 46 in the top of the central portion of the second (lower) diaphragm 40. Therefore, since the bleed rate of pressure from the central pressure chamber 35 is substantially constant as hereinbefore discussed, the bleed rate of pressure from the blood pressure cuff 100 is also be substantially constant. Further, since the bleed rate of pressure from the blood pressure cuff 100, that is the cuff pressure decrease rate, is established by the bleed rate of pressure from the fixed volume central pressure chamber 35, the deflation rate of the cuff 100 is independent of the volume of the first pressure chamber 25 and of the associated blood pressure cuff 100. Thus, when the bleed valve assembly 10 of the invention is used, whether the blood pressure cuff 100 is a large adult cuff or a much smaller child's cuff, the cuff deflation rate is effectively the same.

In the bleed valve assembly 10 of the invention, the magnitude of the cuff deflation rate is set by the initial axial placement of the tapered tip 82 of the rod 80 relative to the second (lower) flexible diaphragm 40 in its unflexed state. For example, in the exemplary embodiment depicted in FIG. 5, the tapered tip 82 of the rod 80 is placed nearly at the top edge of the hole 46 in the central portion of the second flexible diaphragm 40. In this position, a particular magnitude for the bleed rate of pressure from the lower pressure chamber 45 is established as the diaphragm 40 moves upwardly after the start of the cuff deflation mode. If it is desired to increase the bleed rate, the tip of the tapered tip 82 of the rod 80 may be initially set more axially downward, i.e. lower in comparison to the embodiment in FIG. 5, so that the tip does not extend as far into the hole 46. As a result, when the diaphragm 40 moves upwardly during the cuff deflation mode, the flow area through the orifice between the rod 80 and the hole 46 is greater, which results in an increased pressure bleed rate. Conversely, if it is desired to decrease the bleed rate, the tapered tip 82 of the rod 80 may be initially set more axially upward, i.e. higher in comparison to the embodiment in FIG. 5, so that the tapered tip 82 of the rod 80 extends through and beyond the hole 46. As a result, when the diaphragm 40 moves upwardly during the cuff deflation mode, the flow area through the orifice between the rod 80 and the hole 46 is less than in FIG. 5, which results in a reduced pressure bleed rate. Therefore, the initial position of the rod 80 relative to the unflexed second flexible diaphragm may be easily adjusted to establish a cuff pressure decrease rate in the generally desired range of 2-3 millimeters Hg per second.

The behavior of the pressure bleed rate during deflation is determined by the shape of the tapered tip 82. This shape may be conical, axisymmetric but not conical, or non-axisymmetric. The shape can be chosen to achieve a linear/constant/deflation rate or to achieve a rate that increases or decreases as the pressure falls. For example, a more gradual taper produces a rate that decreases as the pressure falls. A more abrupt taper produces a rate that increases as the pressure falls.

Because the blood pressure cuff 100 deflates through the bleed valve assembly 10 of the invention at a substantially constant cuff deflation rate without adjustment by the operator, the operator may concentrate on accurately detecting the systolic and diastolic blood pressure measurements of the patient. Once the diastolic blood pressure measurement has been detected, the operator may reset the control valve 50 to rapidly further deflate the cuff 100 to relieve the pressure exerted by the cuff 100 on the patient's limb, thereby enhancing patient comfort. To do so, the operator resets the control valve 50 to its third position by rotating the disc 53, for example by means of a hand dial (not shown), a further 45 degrees to align the interior passage 57 in registration with the ports 52 and 54 and to simultaneously align the interior passage 59 in registration with the ports 52 and 58, as depicted in FIG. 3. In this position, the interior passage 55 is not in registration with any of the ports of the control valve and is not functional. With the disc 53 so positioned, the blood pressure cuff 100 is now in direct pneumatic communication with ambient pressure via conduits 101 and 103, and via the control valve internal passage 57. Internal passage 57 provides a fluid flow path between the ports 52 and 54. As a result of this direct connection to ambient pressure through the control valve 50, the remaining air in the partially deflated blood pressure cuff 100 bypasses the bleed valve 20 and vents directly to ambient pressure rapidly. Similarly, the central pressure chamber 35 is now also in direct pneumatic communication with ambient pressure via conduit 107, the control valve internal passages 59 and 57. A fluid path between port 58 and port 54 is thereby provided, allowing the air within the central pressure chamber 50 to also vent rapidly directly to ambient pressure.

It is noted that some users might want to temporarily increase the cuff pressure change rate during a portion of the blood pressure measurement process. For example, such a temporary increase could be desired after the systolic pressure has been noted, but while the decreasing cuff pressure is still well above the expected diastolic pressure. This temporary increase could be provided via means for momentarily moving the control valve between the second and third positions. This temporary increase could also be provided via means for momentarily moving the tapered rod axially downward from its normal operative position.

The bleed valve assembly of the invention has been described herein an exemplary embodiment particularly advantageous for use in application to blood pressure measurement manually. However, those skilled in the art will recognize that the bleed valve assembly of the invention is also suitable for use in connection with an electronic blood measurement apparatus. In a preferred embodiment of such an apparatus, the subject valve and a hand pump may be employed. The electronic apparatus would contain an electronic module having a pressure transducer, an oscillometric data processor, and a display. Such an embodiment could be made low cost by avoiding use of a high cost electrical pump and electrically modulated bleed valve. Also, power usage could be low via use of the subject non-electric valve, manual pump, and a low power electronic module. Further, it should be understood that the bleed valve assembly 10 of the invention may also be employed in connection with venting any pressure reservoir wherein it is desired to vent pressure from the reservoir at a substantially constant rate without manual adjustment of a bleed valve.

While the present invention has been particularly shown and described with reference to the preferred mode as illustrated in the drawing, it will be understood by one skilled in the art that various changes in detail may be effected therein without departing from the spirit and scope of the invention as defined by the claims.

I claim:

1. A bleed valve assembly for controlling the pressure change rate in a reservoir under pressure when venting fluid from the reservoir, said bleed valve assembly comprising:
    a bleed valve defining an interior chamber;
    a first flexible diaphragm disposed within and extending across the interior chamber of said bleed valve and sectioning the interior chamber into a first pressure chamber on a front side of said first diaphragm and a second pressure chamber on a rear side of said first diaphragm, said first diaphragm providing a seal between the first pressure chamber and the second pressure chamber, the first pressure chamber connected in direct pneumatic communication with the reservoir;
    a first vent passage between the first pressure chamber of said bleed valve and ambient pressure exterior of said bleed valve, said first vent passage having a regulated flow area;
    a second vent passage between the second pressure chamber of said bleed valve and an outlet, said second vent passage having a variable flow area;
    a selectively positionable control valve operatively associated with, and connected in pneumatic communication with, the interior chamber of said bleed valve, said control valve being selectively positionable in a first position for pressurizing the first pressure chamber, the second pressure chamber, and the reservoir; in a second position for venting the reservoir through the first vent passage and for simultaneously venting the second pressure chamber to ambient pressure through the second vent passage at a substantially constant pressure decrease rate, and in a third position for rapidly venting the reservoir to ambient pressure;
    a second flexible diaphragm disposed within the interior chamber of said bleed valve in spaced relationship with said first diaphragm to establish a third pressure chamber, the second pressure chamber extending between the rear side of said first diaphragm and a front side of said second diaphragm, the third pressure chamber being on a rear side of said second diaphragm, said second diaphragm having a hole passing therethrough providing pneumatic communication between the second pressure chamber and the third pressure chamber; and
    an axially elongated rod having a tapered tip positioned within the hole in said second flexible diaphragm, said second flexible diaphragm being moveable axially in operative association with the tapered tip of said rod to form said variable flow area.

2. A bleed valve assembly as recited in claim 1 wherein said selectively positionable control valve has a first port connected in pneumatic communication with the pressure reservoir and the first pressure chamber of said bleed valve, a second port in pneumatic communication with ambient pressure, a third port in pneumatic communication with the third pressure chamber of said bleed valve, and a fourth port in pneumatic communication with the second pressure chamber of said bleed valve.

3. A bleed valve assembly as recited in claim 2 wherein said selectively positionable control valve is positionable in a first position wherein the first, third and fourth ports are connected in pneumatic communication, a second position wherein the second port and the third port are connected in pneumatic communication, and a third position wherein the first port, the second port, and the fourth port are connected in pneumatic communication.

4. A bleed valve assembly as recited in claim 2 wherein said selectively positionable control valve is positionable to connect the first port, the third port, and the fourth port in pneumatic communication to allow simultaneous pressurization of the reservoir, the first pressure chamber, the second pressure chamber, and third pressure chamber of said bleed valve.

5. A bleed valve assembly as recited in claim 2 wherein said selectively positionable control valve is positionable to connect the second port and the third port of said bleed valve in pneumatic communication to allow venting the reservoir through the first pressure chamber of said bleed valve at a substantially constant pressure decrease rate.

6. A bleed valve assembly as recited in claim 2 wherein said selectively positionable control valve is positionable to connect the first port, the second port, and the fourth port of said bleed valve in pneumatic communication to allow venting the reservoir to ambient pressure at an accelerated bleed rate relative to the substantially constant pressure decrease rate.

7. A bleed valve assembly as recited in claim 1 wherein said axially elongated rod is selectively positioned axially within the hole in said second flexible diaphragm to provide an annular orifice between said rod and said second flexible diaphragm having a desired maximum flow area when said second flexible diaphragm is in an unflexed state.

8. A bleed valve assembly as recited in claim 1 wherein the tapered distal tip of said axially elongated rod comprises an extension of said rod that tapers from a maximum cross-sectional area at a proximal base end to a minimum cross-sectional area at a distal end.

9. A bleed valve assembly for controlling the pressure rate of change in an inflated blood pressure cuff when deflating the cuff, said bleed valve assembly comprising:
   a bleed valve defining an interior chamber;
   a first flexible diaphragm disposed within and extending across the interior chamber of said bleed valve and sectioning the interior chamber into a first pressure chamber on a front side of said first diaphragm and a second pressure chamber on a rear side of said first diaphragm, said first diaphragm providing a seal between the first pressure chamber and the second pressure chamber, the first pressure chamber connected in direct pneumatic communication with the cuff;
   a first vent passage between the first pressure chamber of said bleed valve and ambient pressure exterior of said bleed valve, said first vent passage having a regulated flow area;
   a second vent passage between the second pressure chamber of said bleed valve and an outlet, said second vent passage having a variable flow area;
   a selectively positionable control valve operatively associated with, and connected in pneumatic communication with, the interior chamber of said bleed valve, said control valve being selectively positionable in a first position for pressurizing the first pressure chamber, the second pressure chamber, and the cuff; in a second position for venting the blood pressure cuff to ambient pressure through the first vent passage and for simultaneously venting the second pressure chamber to ambient pressure through the second vent passage at a substantially constant pressure decrease rate, and in a third position for rapidly venting the blood pressure cuff to ambient pressure;
   a second flexible diaphragm disposed within the interior chamber of said bleed valve in spaced relationship with said first diaphragm to establish a third pressure chamber, the second pressure chamber extending between the rear side of said first diaphragm and a front side of said second diaphragm, the third pressure chamber being on a rear side of said second diaphragm, said second diaphragm having a hole passing therethrough providing pneumatic communication between the second pressure chamber and the third pressure chamber; and
   an axially elongated rod having a tapered tip positioned within the hole in said second flexible diaphragm, said second flexible diaphragm being moveable axially in operative association with the tapered tip of said rod to form said variable flow area.

10. A bleed valve assembly as recited in claim 9 wherein said selectively positionable control valve has a first port connected in pneumatic communication with the blood pressure cuff and the first pressure chamber of said bleed valve, a second port in pneumatic communication with ambient pressure, a third port in pneumatic communication with the third pressure chamber of said bleed valve, and a fourth port in pneumatic communication with the second pressure chamber of said bleed valve.

11. A bleed valve assembly as recited in claim 10 wherein said selectively positionable control valve is positionable in a first position wherein the first, third and fourth ports are connected in pneumatic communication, a second position wherein the second port and the third port are connected in pneumatic communication, and a third position wherein the first port, the second port, and the fourth port are connected in pneumatic communication.

12. A bleed valve assembly as recited in claim 10 wherein said selectively positionable control valve is positionable to connect the first port, the third port, and the fourth port in pneumatic communication to allow simultaneous pressurization of the blood pressure cuff, the first pressure chamber, the second pressure chamber, and third pressure chamber of said bleed valve.

13. A bleed valve assembly as recited in claim 10 wherein said selectively positionable control valve is positionable to connect the second port and the third port of said bleed valve in pneumatic communication to allow venting the blood pressure cuff through the first pressure chamber of said bleed valve at a substantially constant pressure decrease rate.

14. A bleed valve assembly as recited in claim 10 wherein said selectively positionable control valve is positionable to connect the first port, the second port, and the fourth port of said bleed valve in pneumatic communication to allow venting the blood pressure cuff to ambient pressure at an accelerated bleed rate relative to the substantially constant pressure decrease rate.

15. A bleed valve assembly as recited in claim 9 wherein said axially elongated rod is selectively positioned axially within the hole in said second flexible diaphragm to provide an annular orifice between said rod and said second flexible diaphragm having a desired maximum flow area when said second flexible diaphragm is in an unflexed state.

16. A bleed valve assembly as recited in claim 9 wherein the tapered distal tip of said axially elongated rod comprises an extension of said rod that tapers from a maximum cross-sectional area at a proximal base end to a minimum cross-sectional area diameter at a distal end.

* * * * *